United States Patent [19]

Koelmel et al.

[11] Patent Number: 4,546,152

[45] Date of Patent: Oct. 8, 1985

[54] POLY(P-DIOXANONE) POLYMERS HAVING IMPROVED RADIATION RESISTANCE

[75] Inventors: Donald F. Koelmel, Lebanon; Dennis D. Jamiolkowski, Long Valley; Shalaby W. Shalaby, Lebanon; Rao S. Bezwada, Whitehouse Station, all of N.J.

[73] Assignee: Ethicon, Inc., Somerville, N.J.

[21] Appl. No.: 587,332

[22] Filed: Mar. 7, 1984

[51] Int. Cl.$^4$ .............................................. C08G 63/66
[52] U.S. Cl. ................................ 525/437; 128/334 R; 128/335.5
[58] Field of Search ............... 525/417, 419, 437, 444, 525/448; 528/173, 176, 193, 194, 195, 206, 207, 209, 295

[56] References Cited

U.S. PATENT DOCUMENTS 4,035,356 7/1977 Jackson, Jr. et al. ............... 528/209
4,052,988 10/1977 Doddi et al. ...................... 128/335.5
4,440,922 4/1984 Barbee et al. ....................... 528/209

*Primary Examiner*—Lester L. Lee
*Attorney, Agent, or Firm*—Charles J. Metz

[57] ABSTRACT

An absorbable, radiation sterilizable, normally solid polymer comprising a copolyester that comprises repeating divalent units of the formulas:

(A) —O—CO—CH$_2$—O—CH$_2$CH$_2$—, and
(B) —G—, and
(C) —O—CO—CHR—O—$_m$Ph—O—CHR—CO—O— wherein G represents the residue after removal of the hydroxyl groups of a dihydric alcohol, wherein Ph represents 1,2-, 1,3-, or 1,4-phenylene or alkyl- or alkoxy-substituted phenylene, wherein m represents a number having a value of 0 or 1, wherein R represents hydrogen or lower alkyl, and wherein the divalent units (A), (B), and (C) are bonded to each other through ester groups contained in said units.

19 Claims, No Drawings

POLY(P-DIOXANONE) POLYMERS HAVING IMPROVED RADIATION RESISTANCE

The invention relates to polyers made from p-dioxanone, and to the valuable surgical products that can be made therefrom. The polymers have enhanced radiation resistance and other valuable attributes.

BACKGROUND OF THE INVENTION

Synthetic absorbable polymers have been used to produce various surgical products such as sutures, implants, prostheses, and the like, for several years. Illustrative U.S. Patents that disclose such polymers are U.S. Pat. Nos. 3,297,033, 3,044,942, 3,371,069, 3,531,561, 3,636,956, Re. 30,170, and 4,052,988.

Implantable surgical devices must be sterile prior to implanting in the body. Sterilization of devices is usually accomplished by the use of heat, ethylene oxide, or gamma radiation using a $^{60}$Co source. In many cases, the use of gamma radiation is the most convenient and most certain way to effect sterilization. However, all of the synthetic absorbable polymers now in commercial use are degraded at least some extent by gamma radiation. Therefore, unless for some reason degradation of the polymer is desired (for instance, to accelerate the absorption rate), the use of gamma radiation is ordinarily precluded for the purpose of sterilizing the presently commercial synthetic absorbable polymers.

This invention provides a new class of polymers that are absorbable and which can be sterilized by gamma radiation while still retaining a desirable level of physical and biological properties.

SUMMARY OF THE INVENTION

The polymers provided by the invention are derived from p-dioxanone, and certain moieties that impart enhanced resistance to degradation by gamma radiation. The polymers of the invention are copolyesters that comprise repeating divalent units of the formulas:
(A) —O—CO—CH$_2$—O—CH$_2$—CH$_2$—, and
(B) —G—, and
(C) —O—CO—(CHR—O—)$_m$—Ph—O—CHR—CO—O—
wherein G represents the residue after removal of the hydroxyl groups of a dihydric alcohol, wherein Ph represents phenylene or alkyl- or alkoxy-substituted phenylene, and wherein m represents a number having a value of 0 or 1, wherein each R individually represents hydrogen or lower alkyl, and wherein the divalent units (A), (B), and (C) are bonded to each other through ester groups formed by linking said units. These polymers are useful in the production of surgical products such as sutures, ligating clips, and the like.

THE PRIOR ART

Kito et al., in Kogyo Kagaku Zasshi 1971, 74 (11), 2313-15 (CA 76, 45892c, 1972), report the preparation of ω-(p-carboxyphenoxy)alkanoic acids and their dimethyl esters.

U.S. Pat. No. 3,637,595 discloses liquid crystal copolyesters prepared from terephthalic acid, hydroquinone, and p-hydroxybenzoic acid. British Pat. Nos. 1,507,207 and 1,508,646 (equivalent to German OS No. 2,520,820) disclose liquid crystal polyesters prepared from a variety of dihydric phenols and aromatic dicarboxylic acids.

In Shalaby et al., U.S. patent application Ser. No. 329,331, filed June 29, 1982 and assigned to the same assignee as this application, there is disclosed radiation sterilizable, absorbable polymers derived from 1,4-phenylene-bis-oxyacetic acid, including copolymers derived from poly(alkylene 1,4-phenylene-bis-oxyacetate) and glycolide and/or lactide.

In Bezwada et al., U.S. patent application Ser. No. 459,428, filed Jan. 20, 1983 now U.S. Pat. No. 4,510,295, and assigned to the same assignee as this application, there is disclosed radiation sterilizable, absorbable polymers derived from 4-(carboxymethoxy)benzoic acid and glycolide and/or lactide.

U.S. Pat. No. 2,516,955 (Butler et al.) discloses esters of phenylene-bis-oxyacetic acid and monohydric alcohols.

Low molecular weight polyesters of phenylene-bis-oxyacetic acid are claimed to have been produced by Spanagel and Carouthers, as reported in JACS, 57, pages 935-936 (1935).

Doddi et al., in U.S. Pat. No. 4,052,988, discloses synthetic absorbable sutures and other surgical devices produced from polymers of p-dioxanone.

DETAILED DESCRIPTION OF THE INVENTION

The polymers of the invention are copolyesters that are preferably produced by the reaction of (a) p-dioxanone monomer, and (b) a base polyester of a dihydric alcohol and a phenylene-bis-oxyacetic acid and/or a carboxymethoxybenzoic acid.

The preferred procedures for the preparation of the base polyesters and the diacids or diesters used to make them are illustrated by Examples 1-9:

EXAMPLE 1

Preparation of Dimethyl Ester of 4-(carboxymethoxy)benzoic Acid

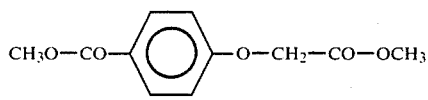

I.

152.2 Grams (1 mole) of methyl p-hydroxybenzoate, 130.2 grams (1.2 mole) of methyl chloroacetate, and 427 milliliters of anhydrous methanol are charged into a 2-liter, 3-neck, round bottom flask fitted with an addition funnel with a nitrogen inlet, a mechanical stirrer, a reflux condenser with a drying tube, a thermometer, and a heating mantle. The reaction mixture is refluxed for 30-60 minutes. A solution of sodium methoxide in methanol (216.1 grams, 25% by weight, or 1 mole of sodium methoxide) is added through the addition funnel in 1-2 hours at reflux. After the addition is completed, the stirred reaction mixture is refluxed for about 16 hours under nitrogen. One milliliter of glacial acetic acid is added to make sure that the reaction mixture is not basic. The hot solution is then filtered to remove the precipitated sodium chloride. Upon cooling the mother liquor, white crystalline material is precipitated. The crystals are filtered, dried, and are then recrystallized twice from anhydrous methanol using 3.5 milliliters per gram of dried product. The product has a melting point of 94°-95.5° C. with an overall yield of 163 grams of the dimethyl ester of 4-(carboxymethoxy)benzoic acid (72.7%).

The corresponding 1,2- and 1,3-isomers are derived by analogous procedures from methyl salicylate and methyl m-hydroxybenzoate, respectively. In those aspects of the invention wherein R in the divalent unit (C) is alkyl, a substituted alpha-chloroacetic ester is used in place of methyl chloroacetate. Examples include methyl alpha-chloropropionate, methyl alpha-chlorobutyrate, and methyl alpha-chlorohexanoate.

The benzene ring in the hydroxybenzoic acid starting reactant can contain substituent groups such as lower alkyl (e.g., methyl) or lower alkoxy (e.g., methoxy) that do not interfere with the esterification reactions to which the monomer will be subjected in producing the copolyester of the invention.

EXAMPLE 2

Preparation of Dimethyl 1,4-Phenylene-bis-oxyacetate

A dry 5-liter, 3-neck round bottom flask equipped with an addition funnel with a nitrogen inlet, a mechanical stirrer, and a reflux condenser with drying tube, a thermometer and a heating mantle is charged with 330.3 grams (3 moles) of hydroquinone, 651.2 grams (6 moles) of methyl chloroacetate, and 1722 ml. of methanol. The contents of the flask are brought to reflux (approximately 68° C.) after an initial purge with nitrogen. A solution of sodium methoxide in methanol (1183 grams, 27.4 weight percent or 6 moles of sodium methoxide), is charged to the addition funnel and allowed to slowly enter the refluxing reaction solution over the course of approximately one hour.

After the addition is completed, the reaction mixture is allowed to reflux an additional 17 hours during which time the reflux temperature drops to 65° C. Glacial acetic acid (about 2 milliliters) is added to make sure the solution is not basic. The solution is filtered while hot (above 60° C.) to remove the precipitated sodium chloride. The filtrate is cooled and a white crystalline material precipitates. The crystals are filtered and a dry weight of 498.9 grams is obtained. The crystals are twice recrystallized from methanol using 4 ml of methanol per gram of dry weight of crystals to result in dimethyl 1,4-phenylene-bis-oxyacetate having a melting point of 97°–98° C., with an overall yield of at least 55.4%.

Just as was the case with the aspect of the invention illustrated by Example 1, a substituted alpha-chloracetic acid ester can be used to produce polymers wherein R in (C) is alkyl.

EXAMPLE 3

Preparation of the dimethyl ester of 1,3-phenylene-bis-oxyacetate

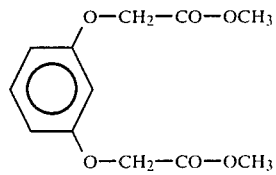

A dry 3-liter, 3-neck, round bottom flask equipped with an addition funnel, a nitrogen inlet, a reflux condenser with a drying tube, and a mechanical stirrer, is charged with 220.2 grams (2 moles) of resorcinol, 434.1 grams (4 moles) of methyl chloroacetate, and 798 milliliters of methanol. The contents of the flask are heated to reflux for 30 minutes after an initial purge with nitrogen. A solution of sodium methoxide in methanol (864.3 grams, 25.0 weight percent or 4 moles of sodium methoxide) is charged to the addition funnel, and added slowly to the refluxing reaction solution over the course of approximately two hours.

After the addition is completed, the reaction mixture is allowed to reflux an additional 17 hours. Two milliliters of glacial acetic acid is added to render the reaction mixture mildly acidic. The solution is hot filtered to remove the sodium chloride. Upon cooling the filtrate, white crystalline material is precipitated. The crystals are filtered and a dry weight of 296.0 grams is obtained. The crystals are recrystallized using 3 milliliters of methanol per gram of dry weight of crystals to result in 134 grams of product. It was recrystallized again using 2 milliliters of methanol per gram of dry crystals to result in dimethyl 1,3-phenylene-bis-oxyacetate having a melting point of 60.5°–61.5° C. and with an overall yield of 24.4 percent.

Preparation of Base Polyester

The base polyesters can be produced by a transesterification or an esterification reaction between a dihydric alcohol of Formula II:

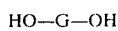

and a compound of Formula III:

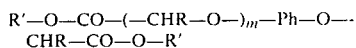

wherein G, Ph, and m have the meanings set forth above, and wherein R is hydrogen or lower alkyl such as methyl, ethyl, or propyl, and wherein R' is hydrogen, lower alkyl such as methyl, ethyl, or isopropyl, or phenyl.

The dihydric alcohols that can be employed to produce the base polyesters, which can be used singly or in mixtures, include $C_2$ to $C_8$ alkylene glycols such as ethylene glycol, 1,2- and 1,3-propylene glycol, 1,4-butylene glycol, 1,6-hexylene glycol, and the like; polyalkylene glycols such as diethylene glycol, triethylene glycol, poly(oxytetramethylene) glycol, and the like; cycloaliphatic diols such as 1,4-cyclohexanedimethanol, and the like; and aromatic dihydric alcohols such as 1,4-bis(2-hydroxyethoxy)benzene, and the like. The polymethylene glycols having three to six carbon atoms are preferred. 1,3-Propylene glycol is most preferred.

The compounds of Formula III are preferably lower alkyl diesters such as the dimethyl diesters, because they are the most convenient to use in a transesterification reaction. The corresponding half esters or diacids can also be used, if desired, but are usually not preferred.

The dihydric alcohol and the diester (or half ester or diacid) are usually reacted in proportions of from about 1.1 to about 4 moles of dihydric alcohol per mole of diester (or half ester or diacid).

A catalytically effective amount of a transesterification catalyst, with or without an esterification catalyst, is used in the reaction. While the reaction would proceed with a wide variety of such catalysts, as a practical matter because the polymers of the invention are intended for use in absorbable products, biologically acceptable catalysts used in very small amounts are preferred. Specific examples of such catalysts are stannous octoate and dibutyltin oxide. Illustrative proportions are from about 750 to about 30,000, and preferably about 1500 to about 15,000 moles of monomer (i.e., moles of the compound of Formula III) per mole of catalyst.

EXAMPLE 4

Preparation of polyester of 1,3-propylene glycol and 1,4-phenylene-bis-oxyacetic acid

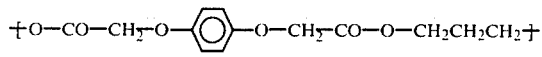

Under a dry nitrogen atmosphere, the following materials were charged into a flame and vacuum dried, two-liter, three-neck, round bottom flask, equipped with a vacuum tight stainless steel paddle stirrer, a short distillation head fitted with a receiver, and an adapter with a hose connection:

444.5 grams Dimethyl 1,4-Phenylene-bis-oxyacetate (1.75 moles)
336.8 grams 1,3-Propanediol (4.42 moles)
0.0253 gram Stannous Octoate ($6.25 \times 10^{-5}$ mole)
(In this Example and in other Examples where it is used, the stannous octoate is added as a solution in toluene.)

After stoppering the flask, the contents of the flask were purged with nitrogen and then subjected to reduced pressure for several hours. The charged reaction vessel was then vented with nitrogen, closed off, and placed in an oil bath. Under nitrogen at one atmosphere pressure, the reaction mixture was melted using a bath temperature of 120° C.

Once the charge was liquified, the reaction flask was connected to an efficient mechanical stirrer and thorough mixing at 120° C. was performed for one-half hour. While still under an atmosphere of nitrogen, the molten reactants were subjected to the following heating sequence: 160° C. for 1.25 hours; 175° C. for 1.5 hours; 190° C. for 2.5 hours; 205° C. for 2 hours; and 220° C. for 2.25 hours.

After the 2.25 hours at 220° C., the receiver containing the distillate was replaced with an empty receiver. Gradually over the course of 0.75 hour, the pressure in the reaction vessel was reduced to 0.05 millimeter of mercury. Under reduced pressure, the reaction mixture was heated at 220° C. for a total of 22.5 hours. The reaction flask was removed from the oil bath, equilibrated with nitrogen, and then allowed to cool to room temperature. The soft polymer was isolated by first chilling the flask in liquid nitrogen to freeze the polymer, breaking the flask, and collecting the frozen polymer.

The polyester was amorphous and had an inherent viscosity of 0.84 dl/gm, measured at 25° C. at a concentration of 0.1 gm/dl in hexafluoroisopropyl alcohol ("HFIP").

EXAMPLE 5

Preparation of polyester of 1,3-propylene glycol and 1,4-phenylene-bis-oxyacetic acid Under a dry nitrogen atmosphere, the following materials were charged to a flame and vacuum dried, one-liter, three-neck, round bottom flask, equipped with a vacuum tight stainless steel paddle stirrer, a short distillation head fitted with a receiver, and an adapter with a hose connection:

254 grams Dimethyl 1,4-phenylene-bis-oxyacetate (1.0 mole)
190.2 grams 1,3-Propanediol (2.5 moles)
0.0144 gram Stannous Octoate ($3.56 \times 10^{-5}$ mole)

After stoppering the flask, the contents of the flask were purged with nitrogen and then subjected to reduced pressure for several hours. The charged reaction vessel was then vented with nitrogen, closed off, and then placed in an oil bath. Under nitrogen at one atmosphere pressure, the reaction mixture was melted using a bath temperature of 120° C. Once the charge was liquified, the reaction flask was connected to an efficient mechanical stirrer and thorough mixing at 120° C. was performed for one-half hour. While still under an atmosphere of nitrogen, the molten reaction mixture was subjected to the following heating sequence: 160° C. for 1.0 hour; 175° C. for 1.0 hour; 190° C. for 2.0 hours; 205° C. for 2.5 hours; and 220° C. for 2.0 hours.

After the 2.0 hours at 220° C., the receiver containing the distillate was replaced with an empty receiver. Gradually over the course of 0.75 hour, the pressure in the reaction vessel was reduced to 0.05 millimeter of mercury. Under reduced pressure, the reaction mixture was heated at 220° C. for a total of 11.25 hours. After this step, the reaction flask was removed from the oil bath, equilibrated with nitrogen, and then allowed to cool to room temperature. The soft polymer was isolated after chilling in liquid nitrogen as described above.

The polyester was amorphous and had an inherent viscosity of 0.81 dl/gm in HFIP.

EXAMPLE 6

Preparation of Polyester of 1,6-hexanediol and 1,4-phenylene-bis-oxyacetic acid

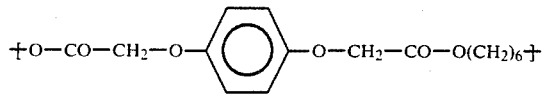

Under a dry nitrogen atmosphere, the following materials were charged to a flame and vacuum dried, 250-ml, round bottom flask, equipped with a vacuum tight stainless steel paddle stirrer, a short distillation head fitted with a receiver, and an adapter fitted with a hose connection:

50.8 grams Dimethyl 1,4-phenylene-bis-oxyacetate (0.20 mole)
24.8 grams 1,6-Hexanediol (0.21 mole)
0.0036 gram Dibutyltin Oxide ($1.45 \times 10^{-5}$ mole).

After stoppering the flask, the contents of the flask were purged with nitrogen and then subjected to reduced pressure for several hours. The charged reaction vessel was then vented with nitrogen, closed off, and placed in an oil bath. While under nitrogen at one atmosphere, the stirred molten reactants were subjected to the following heating sequence: 160° C. for 1.5 hours; 190° C. for 0.5 hour; and 220° C. for 1.0 hour.

After the 1.0 hour at 220° C., the receiver containing the distillate was replaced with an empty receiver. Gradually over the course of 0.75 hour, the pressure in the reaction vessel was reduced to 0.05 millimeter of mercury. Under reduced pressure, the reaction mixture was heated at 220° C. for 1.5 hours and at 230° C. for 3.5 hours. After this step, the reaction flask was removed from the oil bath, equilibrated with nitrogen, and then allowed to cool to room temperature. The soft polymer was isolated after chilling in liquid nitrogen, as described above. The polyester had a melting point of 65°–70° C. and an inherent viscosity of 0.36 dl/gm in HFIP.

EXAMPLE 7

Preparation of Polyester of 1,6-hexanediol and 1,4-phenylene-bis-oxyacetic acid

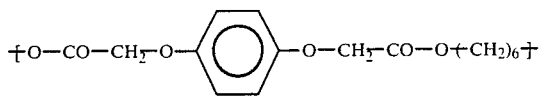

Under a dry nitrogen atmosphere, the following materials were charged to a flame and vacuum dried, 250-ml, two-neck, round bottom flask, equipped with a vacuum tight stainless steel paddle stirrer, a short distillation head fitted with a receiver, and an adapter fitted with a hose connection:
50.8 grams Dimethyl 1,4-Phenylene-bis-oxyacetate (0.20 mole)
24.8 grams 1,6-hexanediol (0.21 mole)
0.0036 gram Dibutyltin Oxide ($1.45 \times 10^{-5}$ mole).

After stoppering the flask, the contents were purged with nitrogen and then exposed to reduced pressure for several hours. The charged reaction vessel was vented with nitrogen, closed off, and placed in an oil bath. Under an atmosphere of nitrogen, the reaction mixture was melted using a bath temperature of 120° C. Once the charge was liquified, the reaction flask was connected to an efficient mechanical stirrer and thorough mixing at 120° C. was performed for one-half hour. While still under nitrogen, the molten reactants were subjected to the following heating sequence: 160° C. for 1.5 hours; 190° C. for 0.5 hours; and 220° C. for 1.0 hour.

After the 1.0 hour at 220° C., the receiver containing the distillate was replaced with an empty receiver. Then gradually over the course of 0.75 hour, the pressure in the reaction vessel was reduced to 0.05 millimeter of mercury. Under reduced pressure, the reaction mixture was heated at 220° C. for 1.0 hour. After this step, the reaction flask was removed from the oil bath, equilibrated with nitrogen, and then allowed to cool to room temperature. The soft polymer was isolated after chilling in liquid nitrogen as described above. The polyester had a melting point of 70°–75° C. and an inherent viscosity in HFIP of 0.63 dl/gm.

EXAMPLE 8

Preparation of Polyester From 1,3-Propanediol and dimethyl 1,3-phenylene-bis-oxyacetate

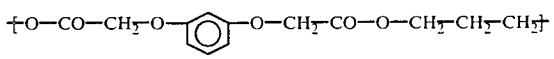

A flame dried, mechanically stirred, 250-milliliter glass reactor (suitable for polycondensation reaction) is charged with 63.6 grams (0.25 mole) of dimethyl 1,3-phenylene-bis-oxyacetate, 57.1 grams (0.75 mole) of 1,3-propanediol, and 0.114 ml. of 0.33M stannous octoate in toluene (0.015 mole percent based on the diester monomer). After purging the reactor and venting with nitrogen, the contents of the reaction flask are melted using an oil bath temperature of 165° C. The temperature of the oil bath is raised to 210° C. in 30 minutes and is maintained at 210° C. for 2 hours, and at 220° C. for 3 hours while still under a nitrogen atmosphere, during which time the methanol formed is collected. The reactor is allowed to cool to room temperature overnight. The next day, the reaction flask is heated slowly under reduced pressure (0.015–1.0 mm) to 210° C. within 6 to 8 hours, and is maintained for 4 hours at 210° C., during which time the distillates are collected. The polymer is isolated, ground, and dried in a vacuum oven at room temperature. The resulting polymer has an inherent viscosity of 0.60 dl/g in hexafluoroisopropyl alcohol at 25° C. and 0.1 g/dl concentration.

EXAMPLE 9

Preparation of polyester of 1,3-propanediol and 4-(carboxymethoxy)benzoic acid

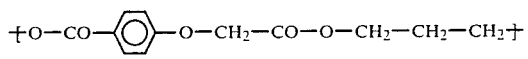

A flame dried, mechanically stirred, 100-milliliter glass reactor (suitable for polycondensation reactions) is charged with 89.7 grams (0.4 mole) of the dimethyl ester of 4-(carboxymethoxy)benzoic acid, 76.10 grams (1.0 mole) of 1,3-propanediol, and 7.16 milligrams of dibutyltin oxide. After purging the reactor and venting with nitrogen, the contents of the reaction flask are melted in an oil bath at 160° C. The temperature of the oil bath is raised to 190° C. in 2 hours and is maintained at 190° C. for 2 hours and then at 210° C. for 2 hours, during which time the methanol formed is collected. The reactor is allowed to cool to room temperature overnight. The next day, the reaction flask is heated slowly under reduced pressure (0.05–1.0 mm) to 210° C. within 3 hours and 30 minutes, and is maintained for 4 hours and 15 minutes at 210° C., during which time the distillates are collected. The polymer is isolated, ground, and dried in a vacuum oven at room temperature. The resulting polymer has an inherent viscosity of 0.58 dl/g in hexafluoroisopropyl alcohol at 25° C. and 0.1 g/dl concentration.

The base polyesters are usually essentially noncrystalline materials, or display low levels of crystallinity, having molecular weights in excess of about 2000, and having inherent viscosities of at least about 0.2 dl/gm, tested at a concentration of 0.1 gm/dl in hexafluoroisopropyl alcohol at 25° C.

Preparation of Copolyester

The copolyesters of the invention are produced by reacting the base polyester with p-dioxanone. The co-esterification reaction is preferably carried out by dissolving the polyester in p-dioxanone, and then subjecting the reaction mixture to elevated temperature for a period of time sufficient to produce the copolyester of the invention. An additional esterification catalyst system may be added for this second polymerization, or the initial catalyst that remains in the reaction mixture from the preparation of the base polyester may be sufficient to catalyze the reaction.

The proportion of polyester to p-dioxanone is selected so that the resulting copolyester will be absorbable and will be able to withstand radiation sterilization while still maintaining a useful level of physical and biological properties. Typically, the copolyester will contain from about 59 to 99 weight percent, and preferably (for suture applications) from 75 to 90 weight percent, of polymerized p-dioxanone. Routine experimentation will suffice to determine the proportions of base polyester and p-dioxanone monomer that should be used in particular cases to achieve the desired proportion in the copolyester product. The Examples herein illustrate typical percent conversions of monomer. It is noted that solid state polymerization (e.g., Example 11) usually yields a higher percent converstion than melt polymerization (e.g., Example 10).

The following Examples 10-19 illustrate the preparation of the copolyesters:

EXAMPLE 10

Preparation of copolyester of p-dioxanone and polyester of 1,3-propanediol and 1,4-phenylene-bis-oxyacetic acid To a dry, 250-milliliter, single-neck, round bottom flask was added 9.0 grams of poly(trimethylene 1,4-phenylene-bis-oxyacetate) having an inherent viscosity in hexafluoroisopropyl alcohol of 0.81 dl/gram (Example 5). The contents of the flask were dried by exposure to high vacuum (less than 0.05 millimeter of mercury) for several hours at room temperature, followed by heating at 110° C. for 16 hours under high vacuum. The following materials were then added to the dried contents of the flask, under a dry nitrogen atmosphere:
57.6 grams p-dioxanone (0.565 mole)
0.0076 gram Stannous Octoate ($1.88 \times 10^{-5}$ mole).

A flame dried vacuum tight stainless steel paddle stirrer and an adapter with a hose connection were attached to the charged reaction flask, and the pressure in the reaction assembly was reduced to a low level for several hours. The reaction flask was then vented with nitrogen, closed off, and placed in an oil bath. Under an atmosphere of dry nitrogen, the reaction mixture was heated, with initially rapid mechanical stirring to facilitate dissolution of the polyester in the monomer, according to the following temperature/time sequence:
80° C./1.75 hrs.
100° C./7.25 hrs.
(The stirring rate was slowed as the viscosity of the polymerizing mass increased.)

The resulting copolyester was isolated after chilling in liquid nitrogen as described above, and then ground. After exposure to vacuum at room temperature for 16 hours, the ground copolyester was heated at 80° C. and a pressure of 0.05 millimeter of mercury for 26 hours to remove unreacted p-dioxanone from the desired copolyester product; a 35.9% weight loss was observed. (Removal of unreacted monomer can also be effected by vented screw extrusion. This latter procedure is preferred when the content of unreacted monomer is relatively high, e.g., over 15 weight percent.) The resulting copolyester product had an inherent viscosity of 1.87 dl/gm measured at 25° C. and a concentration of 0.1 gram/dl in hexafluoroisopropyl alcohol.

EXAMPLE 11

Preparation of copolyester of p-dioxanone and polyester of 1,3-propanediol and 1,4-phenylene-bis-oxyacetic acid To a dry, 100-milliliter, single-neck, round bottom flask was added 4.14 grams of poly(trimethylene 1,4-phenylene-bis-oxyacetate) having an inherent viscosity in hexafluoroisopropyl alcohol of 0.87 dl/gram. The contents of the flask were dried by exposure to high vacuum (less than 0.05 millimeter of mercury) for several hours at room temperature, followed by heating at 90° C. for 15 hours under high vacuum. The following materials were next added to the dried contents of the flask, under a dry nitrogen atmosphere:
23.5 grams p-Dioxanone (0.23 mole)
0.00468 gram Stannous Octoate ($1.16 \times 10^{-5}$ mole).

A flame dried vacuum tight stainless steel paddle stirrer and an adapter with a hose connection were attached to the charged reaction flask, and the pressure in the reaction assembly was reduced to a low level for several hours. The reaction flask was vented with nitrogen, closed off, and placed in an oil bath. Under dry nitrogen at one atmosphere, the reaction mixture was heated, with initially rapid mechanical stirring, according to the following temperature/time sequence:
80° C./1.0 hr.
90° C/27.0 hrs.
80° C./88.0 hrs.
(Stirring was slowed and eventually stopped when the viscosity of the polymerizing mass became so great as to virtually prevent further stirring.)

The resulting copolyester was isolated after chilling in liquid nitrogen as described above, and then ground. After exposure to vacuum at room temperature for 16 hours, the ground copolyester was heated at 80° C. and a pressure of 0.05 millimeter of mercury for 16 hours to remove unreacted p-dioxanone from the desired copolyester product; an 8.6% weight loss was observed. The resulting copolyester product had an inherent viscosity of 1.84 dl/gm measured at 25° C. at a concentration of 0.1 gram/dl in hexafluoroisopropyl alcohol, and a melting point of 105°-111° C. (by thermal microscopy).

EXAMPLE 12

Preparation of copolyester of p-dioxanone and polyester of 1,3-propanediol and 1,4-phenylene-bis-oxyacetic acid To a dry, 250-milliliter, single-neck, round bottom flask was added 9.0 grams of poly(trimethylene 1,4-phenylene-bis-oxyacetate) having an inherent viscosity in hexafluorisopropyl alcohol of 0.63 dl/gram. The contents of the flask were dried by exposure to a high vacuum (less than 0.05 millimeter of mercury) for several hours at room temperature, followed by heating at 90° C. for 12 hours under high vacuum. The following materials were then added to the dried contents of the flask, under a dry nitrogen atmosphere:
81.0 grams p-Dioxanone (0.794 mole)
0.0160 gram Stannous Octoate ($3.96 \times 10^{-5}$ mole).

A flame dried vacuum tight stainless steel paddle stirrer and an adapter with a hose connection were attached to the charged reaction flask, and the pressure in the reaction assembly was reduced to a low level for several hours. The reaction flask was then vented with nitrogen and placed in an oil bath. Under a dry nitrogen atmosphere, the reaction mixture was heated, with initially rapid mechanical stirring, according to the following temperature/time sequence:
80° C./1.0 hr.
90° C./27.0 hrs.
80° C./88.0 hrs.
(Stirring was slowed and eventually stopped when the viscosity of the polymerizing mass became so great as to virtually prevent further stirring.)

The resulting copolyester was isolated after chilling in liquid nitrogen, and was then ground. After exposure to vacuum at room temperature for 16 hours, the ground copolyester was heated at 80° C. and a pressure of 0.05 millimeter of mercury for 16 hours to remove unreacted p-dioxanone from the desired copolyester product; an 11.2% weight loss was observed. The resulting copolyester product had an inherent viscosity of 1.74 dl/gm measured at 25° C. at a concentration of 0.1 gram/dl in hexafluoroisopropyl alcohol, and a melting point (by thermal microscopy) of 107°–111° C.

EXAMPLE 13

Preparation of copolyester of p-dioxanone and polyester of 1,3-propanediol and 1,4-phenylene-bis-oxyacetic acid To a dry, 2-liter, three-neck, round bottom flask was added 75.0 grams of poly(trimethylene 1,4-phenylene-bis-oxyacetate) having an inherent viscosity in hexafluoroisopropyl alcohol of 0.81 dl/gram (Example 5). The contents of the flask were dried by exposure to high vacuum (less than 0.05 millimeter of mercury) for several hours at room temperature, followed by heating at 110° C. for 16 hours under high vacuum. The following materials were added to the dried contents of the flask, under a dry nitrogen atmosphere:
425.0 grams p-Dioxanone (4.17 moles)
0.0842 gram Stannous Octoate ($2.08 \times 10^{-4}$ mole).

A flame dried vacuum tight stainess steel paddle stirrer and an adapter with a hose connection were attached to the charged reaction flask, and the pressure in the reactor was reduced to a low level for several hours. The reaction flask was vented with nitrogen, closed off, and placed in an oil bath. Under a dry nitrogen atmosphere, the reaction mixture was heated, with initially rapid mechanical stirring, according to the following temperature/time sequence:
75° C./2.25 hrs.
90° C./3.0 hrs.
80° C./135 hrs.
(Stirring was slowed and eventually stopped when the viscosity of the polymerizing mass became so great as to virtually prevent further stirring.) The resulting copolyester was isolated after chilling in liquid nitrogen, and then ground. After exposure to vacuum at room temperature for 16 hours, the ground copolyester was heated at 80° C. and a pressure of 0.05 millimeter of mercury for 62 hours to remove unreacted p-dioxanone from the desired copolyester product; an 11.8% weight loss was observed. The resulting copolyester product had an inherent viscosity of 2.18 dl/gm measured at 25° C. and a concentration of 0.1 gram/dl and 25° C. in hexafluoroisopropyl alcohol, and a melting point (by thermal microscopy) of 109°–111° C.

EXAMPLE 14

Preparation of copolyester of p-dioxanone and polyester of 1,6-hexanediol and 1,4-phenylene-bis-oxyacetic acid To a dry, 500-milliliter, single-neck, round bottom flask was added 4.5 grams of poly(hexamethylene 1,4-phenylene-bis-oxyacetate) having an inherent viscosity in hexafluoroisopropyl alcohol of 0.63 dl/gram (Example 7). The contents of the flask were dried by exposure to high vacuum (less than 0.05 millimeter of mercury) for several hours at room temperature, followed by heating at 90° C. for 15 hours under high vacuum. The following materials were added to the dried contents of the flask, under a dry nitrogen atmosphere:
85.5 grams p-Dioxanone (0.838 mole)
0.0170 gram Stannous Octoate ($4.19 \times 10^{-5}$ mole).

A flame dried vacuum tight stainless steel paddle stirrer and an adapter with a hose connection were attached to the charged reaction flask, and the pressure in the reactor was reduced to a low level for several hours. The reaction flask was vented with nitrogen, closed off, and placed in an oil bath. Under a dry nitrogen atmosphere, the reaction mixture was heated, with initially rapid mechanical stirring, according to the following temperature/time sequence:
80° C./1.0 hr.
90° C./27.0 hrs.
80° C./88.0 hrs.
(Stirring was slowed and eventually stopped when the viscosity of the polymerizing mass became so great as to virtually prevent further stirring.)

The resulting copolyester was isolated after chilling in liquid nitrogen, and then ground. After exposure to vacuum at room temperature for 16 hours, the ground copolyester product was heated at 80° C. and a pressure of 0.05 millimeter of mercury for 16 hours to remove unreacted p-dioxanone from the desired copolyester product; a 3.9% weight loss was observed. The resulting copolyester product had an inherent viscosity of 2.29 dl/gm measured at 25° C. at a concentration of 0.1 gram/dl in hexafluoroisopropyl alcohol, and a melting point of 104°–114° C. (by thermal microscopy).

EXAMPLE 15

Preparation of copolyester of p-dioxanone and polyester of 1,6-hexanediol and 1,4-phenylene-bis-oxyacetic acid To a dry, 100-milliliter, single-neck, round bottom flask was added 3.0 grams of poly(hexamethylene 1,4-phenylene-bis-oxyacetate) having an inherent viscosity in hexafluoroisopropyl alcohol of 0.36 dl/gram (Example 6). The contents of the flask were dried by exposure to high vacuum (less than 0.05 millimeter of mercury) for several hours at room temperature, followed by heating at 90° C. for 15 hours under high vacuum. The following materials were added to the dried contents of the flask, under a dry nitrogen atmosphere:
27.0 grams p-Dioxanone (0.265 mole)
0.00534 gram Stannous Octoate $1.32 \times 10^{-5}$ mole).

A flame dried vacuum tight stainless steel paddle stirrer and an adapter with a hose connection were attached to the charged reaction flask, and the pressure in the reactor was reduced to a low level for several hours. The reaction flask was vented with nitrogen, closed off, and placed in an oil bath. Under a dry nitrogen atmosphere, the reaction mixture was heated, with initially rapid mechanical stirring, according to the following temperature/time sequence:
80° C./0.75 hr.
90° C./3.3 hrs.
80° C./112 hrs.
(Stirring was slowed and eventually stopped when the viscosity of the polymerizing mass became so great as to virtually prevent further stirring.)

The resulting copolyester was isolated after chilling in liquid nitrogen, and then ground. After exposure to vacuum at room temperature for 16 hours, the ground copolyester product was heated at 80° C. and a pressure of 0.05 millimeter of mercury for 16 hours to remove unreacted p-dioxanone from the desired copolyester product; a 11.2% weight loss was observed. The copolyester product had an inherent viscosity of 1.82 dl/gm measured at 25° C. at a concentration of 0.1 gram/dl in hexafluoroisopropyl alchol, and a melting point (by thermal microscopy) of 109°–112° C.

EXAMPLE 16

Preparation of coplyester of p-dioxanone and polyester of 1,3-propanediol and 1,3-phenylene-bis-oxyacetic acid A flame dried, 100-milliliter, round bottom, one-neck flask is charged under nitrogen with 5 grams of the polyester of Example 8 and the contents of the flask are held for about 16 hours at 115° C./0.1 mm. To the same flask, after drying, 45 grams of p-dioxanone and 0.58 ml of 0.033M stannous octoate in toluene (0.00434 mole percent, based on p-dioxanone monomer) are charged and then the flask is fitted with a vacuum tight mechanical stirrer. The flask is dried under vacuum and purged with nitrogen three times before being vented with nitrogen and immersed in a silicone oil bath. The mixture is heated to and maintained at about 85° C. with rapid stirring for one hour to melt the p-dioxanone and to dissolve the polyester. The temperature of the oil bath is raised to 90° C. and maintained for 24 hours at 90° C. The mechanical stirring is discontinued after 3 to 4 hours at 90° C. because of the viscous nature of the reaction mass. The temperature of the oil bath is lowered to 80° C. and is maintained there for 72 hours. The polymer is isolated, ground, and dried 18 hours/80° C./0.1 mm to remove any unreacted monomer. A weight loss of 10.1% is observed. The resulting polymer has a melting range of about 104°–107° C. and an inherent viscosity of about 2.2 dl/g at 25° C. and a concentration of 0.1 g/dl in hexafluoroisopropyl alcohol.

EXAMPLE 17

Preparation of copolyester of p-dioxanone and polyester of 1,3-propanediol and 4-(carboxymethoxy)benzoic acid A flame dried, 250 milliliter, round bottom, one-neck flask is charged under nitrogen with 10 grams of the polyester of Example 9 and the flask is held for about 16 hours at 50° C./0.1 mm. To the same flask, after drying, 90 grams of p-dioxanone and 0.133 ml of 0.33M stannous octoate in toluene (0.005 mole percent, based on p-dioxanone monomer) are charged and then the flask is fitted with a mechanical stirrer. The flask is dried under vacuum and purged with nitrogen three times before being vented with nitrogen and immersed in a silicone oil bath. The mixture is heated to and maintained at about 85° C. with rapid stirring for one hour to melt the p-dioxanone and to dissolve the polyester. The temperature of the oil bath is raised to 90° C. and maintained for 24 hours at 90° C. The mechanical stirring is discontinued after 3 to 4 hours at 90° C. because of the viscous nature of the reaction mass. The temperature of the oil bath is lowered to 80° C. and is maintained there for 72 hours. The polymer is isolated, ground, and dried for 36 hours/80° C./0.1 mm to remove any unreacted monomer. A total of 12.72% monomer is removed due to drying. The resulting polymer has a melting range of about 106°–110° C. and an inherent viscosity of about 1.88 dl/g at 25° C. and a concentration of 0.1 g/dl in hexafluoroisopropyl alcohol.

EXAMPLE 18

Preparation of copolyester of p-dioxanone and polyester of 1,3-propanediol and 1,3-phenylene-bis-oxyacetic acid A flame dried, 250-milliliter, round bottom, one-neck flask is charged under nitrogen with 15 grams of the polyester of Example 8 and the contents of the flask are held for about 16 hours at 115° C./0.1 mm. To the same flask, after drying, 85 grams of p-dioxanone and 0.10 milliliter of 0.33M stannous octoate in toluene (0.00396 mole percent based on p-dioxanone monomer) are charged and the flask is fitted with a flame dried mechanical stirrer and an adapter with a hose connection. The reactor is purged with nitrogen three times before being vented with nitrogen. The reactor is connected to a gas supply to maintain nitrogen at a pressure of one atmosphere for the remainder of the run and then is immersed in a silicone oil bath. The mixture is heated to and maintained at about 80° C. for one hour to melt the p-dioxanone and to dissolve the polyester. The temperature of the oil bath is raised to 90° C. and is maintained there for 24 hours. The mechanical stirring is discontinued after 3 to 4 hours at 90° C. because of the viscous nature of the reaction mass. The temperature of the oil bath is lowered to 80° C. and maintained there for 72 hours. The polymer is isolated, ground, and dried 18 hours/80° C./0.1 mm to remove any unreacted monomer. A weight loss of 12.8% is observed. The resulting polymer has a melting range of about 105°–108° C. and an inherent viscosity of about 1.82 dl/g at 25° C. and a concentration of 0.1 g/dl in hexafluoroisopropyl alcohol.

EXAMPLE 19

Preparation of copolyester of p-dioxanone and polyester of 1,3-propanediol and 4-(carboxymethoxy)benzoic acid A flame dried, 250-milliliter, round bottom, one-neck flask is charged under nitrogen with 15 grams of the polyester of Example 9 and the flask is held for about 16 hours at 50° C./0.1 mm. To the same flask, after drying, 85 grams of p-dioxanone and 0.126 milliliter of 0.33M stannous octoate in toluene (0.005 mole percent, based on p-dioxanone monomer) are charged and the flask is fitted with a mechanical stirrer and an adapter with a hose connection. The reactor is purged with nitrogen three times before being vented with nitrogen. The reactor is connected to a gas supply to maintain nitrogen at a pressure of one atmosphere for the remainder of the run and then is immersed in a silicone oil bath. The mixture is heated to and maintained at about 75° C. for one hour to melt the p-dioxanone and to dissolve the polyester. The temperature of the oil bath is raised to 90° C. and is maintained there for 24 hours. The mechanical stirring is discontinued after 3 to 4 hours at 90°

C. because of the viscous nature of the reaction mass. The temperature of the oil bath is lowered to 80° C. and is maintained there for 72 hours. The polymer is isolated, ground, and dried for 18 hours/80° C./0.1 mm to remove any unreacted monomer. A total of 5.79% monomer is removed. The resulting polymer has a melting range of about 107°–109° C. and an inherent viscosity of about 1.56 dl/g at 25° C. and a concentration of 0.1 g/dl in hexafluoroisopropyl alchol.

Control 1

Under a dry nitrogen atmosphere, p-dioxanone (155.2 grams, 1.52 moles), 1-dodecanol (0.473 gram, 2.54 millimoles, 4.73 milliters of a 0.537 M toluene solution), and a catalytic amount of stannous octoate (0.115 milliliter of a 0.33 M toluene solution, 0.038 millimoles) were added to a flame and vacuum dried 500 milliliter glass ampoule, equipped with a magnetic stirring bar. The contents of the ampoule were exposed to vacuum at room temperature for several hours with intermittant dry nitrogen purges. The glass ampoule was sealed under partial vacuum, placed in a silicone oil bath, and its contents heated (with rapid magnetic mixing as melting viscosity allowed) according to the following temperature/time scheme:
120° C./1 Minute
90° C./3 Hours
80° C./96 Hours.

The resulting polyester was isolated by immersing the glass ampoule in liquid nitrogen and shattering the surrounding glass with a heavy object. The glass-free polymer was ground in a Wiley mill and stored under vacuum for 16 hours at room temperature. The ground polymer was heated at 80° C. under a pressure of 0.05 millimeters of mercury for 16 hours to remove any unreacted p-dioxanone. The polyester possessed an inherent viscosity of 1.79 dl/gm measured at 25° C. and a concentration of 0.1 gram/dl in hexafluoroisopropyl alcohol.

The control polyester was spun at 155° C. at a shear rate of 213 sec$^{-1}$ using an INSTRON Capillary Rheometer with a 40 mil die (L/D=24.1) and a ram speed of 2 cm/min. An apparent melt viscosity of 6715 poise was observed. The fiber was taken up at 24 feet/minute after an ice water quench; the wound fiber was dried and subsequently drawn one week later.

The control extrudate (diameter range: 17.0 to 18.5 mils) was drawn in two stages employing a glycerine draw bath under the conditions of 4× at 55° C. followed by 1.5× at 75° C. and subsequently water-washed and dried in vacuo at room temperature.

The control drawn monofilaments were annealed at 77° C. for 6 hours with 5% relaxation.

The control annealed monofilaments were cut to appropriate lengths, placed in individual paper folders and heat-sealable vented foil envelopes. The packages were subjected to 50° C. and 0.1 mm Hg pressure for 72 hours to dry and subsequently sealed under nitrogen. Portions of the control packaged fibers were sterilized by exposure to 2.5Mrads of gamma radiation from a Co$^{60}$ source.

EXTRUSION

The copolyesters are melt extruded through a spinnerette in a conventional manner to form one or more filaments.

Extrusion of the copolyesters described herein was accomplished using an INSTRON Capillary Rheometer. The copolymers were packed in the preheated (80° to 90° C.) extrusion chamber and extruded through a 40 mil die (L/D=24.1) after a dwell time of 11 to 13 minutes at the extrusion temperature and a ram speed of 2 cm/min. While extrusion temperatures depend both on the polymer Tm and on the melt viscosity of the material at a given temperature, extrusion of the subject copolyesters at temperatures of about 10° to 75° C. above the Tm is usually satisfactory. The extrusion temperatures of the example copolyesters described herein ranged from 155° to 185° C. The extrudate was taken up through an ice water quench bath at either 24, 28 or 38.5 feet/minute. A screw-type extruder or similar device can be substituted for the INSTRON Capillary Rheometer.

The extrudate filaments are subsequently drawn about 4× to 7× in a one or multistage drawing process in order to achieve molecular orientation and improve tensile properties. The extrudates described herein were drawn 2 hours to about 1 week after extrusion. (The length of time elapsed between extrusion and drawing may effect the drawing process; the optimum time elapsed is easily determined by simple experimentation for each fiber composition.) The manner of drawing is as follows:

The extrudate (diameter range, 13–20 mils) passed through rollers at an input speed of four feet per minute and into a heated draw bath of glycerine. The temperatures of the draw bath can vary from about 25° to 90° C.; the examples described herein employ temperatures between 52° and 61° C. The draw ratio in this first stage of drawing can vary from 3× to about 7×; the examples described herein employ draw ratios from 4× to 5×. The partially drawn fibers are then placed over a second set of rollers into a glycerine bath (second stage) kept at temperatures ranging from 50° to 95° C.; the examples described herein employ second stage draw temperatures of 69° to 84° C. Draw ratios of up to 2× are applied in this second stage, but a ratio range of from 1.2× to 1.5× has been employed in the examples. The fiber is passed through a water-wash, taken up on a spool, and dried. A set of hot rollers can be substituted for a portion or all of the glycerine draw bath. The resulting oriented filaments have good straight and dry tensile strengths.

Dimensional stability and tensile strength retention of the oriented filaments may be enhanced by subjecting the filaments to an annealing treatment. This optional treatment consists of heating the drawn filaments to a temperature of from about 40° to 90° C., most preferably from about 60° to 80° C. while restraining the filaments to prevent any substantial shrinkage. This process may begin with the filaments initially under tension or with up to 20% shrinkage allowed prior to restraint. The filaments are held at the annealing temperature for a few seconds to several days or longer depending on the temperature and processing conditions. In general, annealing at 60° to 80° C. for up to about 24 hours is satisfactory for the copolyesters of the invention. Optimum annealing time and temperature for maximum fiber in vivo strength retention and dimensional stability is readily determined by simple experimentation for each fiber composition.

The characteristic properties of the filaments of the invention are readily determined by conventional test procedures. The tensile properties (i.e., straight and knot tensile strengths, Young's Modulus, and elongation) displayed herein were determined with an IN- STRON tensile tester. The settings used to determine the straight tensile, knot tensile, break elongation, and Young's Modulus were the following, unless indicated:

|  | Gauge Length (cm) | Chart Speed (cm/min) | Crosshead Speed (cm/min) |
|---|---|---|---|
| Straight Tensile | 12 | 20 | 10 |
| Knot Tensile | 5 | 10 | 10 |
| Break Elongation | 12 | 20 | 10 |
| Young's Modulus | 12 | 20 | 10 |

The straight tensile strength is calculated by dividing the force to break by the initial cross-sectional area of the fiber. The elongation to break is read directly from the stress-strain curve of the sample allotting 4-1/6% per centimeter of horizontal displacement.

Young's Modulus is calculated from the slope of the stress-strain curve of the sample in the linear elastic region as follows:

$$\text{Young's Modulus} = \frac{\tan\theta \times GL \times CS \times SL}{XH \times XS}$$

$\theta$ is the angle between the slope and the horizontal, XS is the initial cross-sectional area of the fiber, SL is the scale load, XH is the crosshead speed, CS is the chart speed, and GL is the gage length. The SL may be selected to provide a $\theta$ close to 45°.

The knot tensile strength of a fiber is determined in separate experiments. The test article is tied into a surgeon's knot with one turn of the filament around flexible tubing of 1/4 inch inside diameter and 1/16 inch wall thickness. The surgeon's knot is a square knot in which the free end is first passed twice, instead of once, through the loop, and the ends drawn taut so that a single knot is superimposed upon a compound knot. The first knot is started with the left end over the right end and sufficient tension is exerted to tie the knot securely.

The specimen is placed in the INSTRON tensile tester with the knot approximately midway between the clamps. The knot tensile strength is calculated by dividing the force required to break by the initial cross-sectional area of the fiber.

Conversion from metric dimensions to English dimensions (i.e. psi) is made by applying the appropriate factors.

EXAMPLE 20

The copolyester of Example 15 is made into monofilament suture material in accordance with the following extrusion, drawing, and annealing conditions:

EXTRUSION

The copolyester was spun at 185° C. at a shear rate of 213 sec$^{-1}$ using an INSTRON Capillary Rheometer with a 40 mil die (L/D=24.1) and a ram speed of 2 cm/min. An apparent melt viscosity of 3000 poise was observed. The fiber was taken up at 24 ft./min after an ice water quench; the wound fiber was dried and subsequently drawn one week later.

DRAWING

The extrudate (diameter range: 17.0 to 18.5 mils) was drawn in two stages employing a glycerine draw bath under the conditions of 4× at 55° C. followed by 1.5× at 73° C. and subsequently water-washed and dried in vacuo at room temperature.

ANNEALING

The drawn monofilament was annealed at 77° C. for 6 hours with 5% relaxation.

The annealed monofilaments were cut to appropriate lengths, placed in individual paper folders and heat-sealable vented foil envelopes. The packages were subjected to 50° C. and 0.1 mm Hg pressure for 72 hours to dry and subsequently sealed under nitrogen. Portions of the packaged fibers were sterilized by exposure to 2.5M rads of gamma radiation from a Co$^{60}$ source. Table I, below, displays representative properties of the dried monofilament, both before and after sterilization, and compares the properties with a typical dried annealed drawn monofilament made from poly(p-dioxanone) homopolymer (Control 1):

TABLE I

| Sample | Diam., Mils | Straight Tensile × 10$^{-3}$, psi | Elong., % | Young's Mod. × 10$^{-3}$, psi | Fiber[1] I.V. |
|---|---|---|---|---|---|
| | | Before Co$^{60}$ Irradiation | | | |
| Example 20 | 8.0 | 56.7 | 43 | 218 | 1.52 |
| Control 1 | 7.8 | 70.9 | 39 | 310 | 1.60 |
| | | After Co$^{60}$ Irradiation | | | |
| Example 20 | 8.1 | 50.4 | 42 | 225 | 1.13 |
| Control 1 | 8.2 | 58.0 | 37 | 301 | 1.21 |

[1]Inherent viscosity of the fiber, tested in HFIP at 25° C. and a concentration of 0.1 gm/dl.

BREAKING STRENGTH RETENTION

The breaking strength retention (BSR) of a fiber is determined by implanting two strands of the fiber in the dorsal subcutis of each of a number of Long-Evans rats. The number of rats used is a function of the number of implantation periods, employing 4 rats per period giving a total of eight (8) examples for each of the periods. Thus 16, 24, or 32 segments of each fiber are implanted corresponding to two, three, or four implantation periods. The periods of in vivo residence are 7, 14, 21, or 28 days. The ratio of the mean value of 8 determinations of the breaking strength (determined with an INSTRON Tensile tester employing the following settings: a gage length of 1 inch, a chart speed of 1 inch/minute, and a crosshead speed of 1 inch/minute) at each period to the mean value (of 8 determinations) obtained for the fiber prior to implantation constitutes its breaking strength retention for that period.

The results of the BSR tests for the packaged and Co$^{60}$ sterilized monofilament of Example 20 are displayed in Table II, compared with the BSR for Control 1 (also packaged and Co$^{60}$ sterilized):

TABLE II

| | | In Vivo Breaking Strength Retention | | | |
|---|---|---|---|---|---|
| | Diam., | Initial | % BSR | | |
| Sample | Mils | Strength, lbs. | 14 | 21 | 28 (days) |
| Example 20 | 8.1 | 2.61 | 62 | 55 | 40 |
| Control 1 | 8.2 | 3.08 | 43 | 30 | 25 |

EXAMPLE 21

The copolyester of Example 14 is made into monofilament suture material in accordance with the following extrusion, drawing, and annealing conditions:

EXTRUSION

The copolyester was spun at 165° C. at a shear rate of 213 sec$^{-1}$ using an INSTRON Capillary Rheometer with a 40 mil die (L/D=24.1) and a ram speed of 2 cm/min. An apparent melt viscosity of 8100 poise was observed. The fiber was taken up at 24 ft/min after an ice water quench; the wound fiber was dried and subsequently drawn six days later.

DRAWING

The extrudate (diameter range: 19.0 to 20.0 mils) was drawn in two stages employing a glycerine draw bath under the conditions of 4× at 58° C. followed by 1.5× and 70° C. and subsequently water-washed and dried in vacuo at room temperature.

ANNEALING

The drawn monofilament was annealed at 80° C. for 6 hours with 5% relaxation.

The annealed monofilament was cut to appropriate lengths, placed in individual paper folders and heat-sealable vented foil envelopes. The packages were subjected to 50° C. and 0.1 mm Hg pressure for 24 hours to dry and subsequently sealed under nitrogen. Portions of the packaged fibers were sterilized by exposure to 2.5M rads of gamma radiation from a Co$^{60}$ source. Table III, below, displays certain physical properties of the annealed monofilament of Example 21 prior to drying and sterilization as well as the in vivo breaking strength retention of the sterilized suture material.

TABLE III

|  | Diam., mils | Tensile, psi | Elong., % | Young's mod., psi |
|---|---|---|---|---|
| Non-Sterile | 8.2 | 73,600 | 30 | 285,000 |

|  | Initial Straight Breaking Strength, lbs. | % BSR | |
|---|---|---|---|
|  |  | 21 | 28 (days) |
| Co$^{60}$ sterilized | 3.95 | 49 | 28 |

EXAMPLE 22

The copolyester of Example 11 is made into monofilament suture material in accordance with the following extrusion, drawing, and annealing conditions:

EXTRUSION

The copolyester was spun at 175° C. at a shear rate of 213 sec$^{-1}$ using an INSTRON Capillary Rheometer with a 40 mil die (L/D=24.1) and a ram speed of 2 cm/min. An apparent melt viscosity of 3800 poise was observed. The fiber was taken up at 38.5 feet/minute after an ice water quench; the wound fiber was dried and subsequently drawn 5 days later.

DRAWING

The extrudate (diameter range: 13.0 to 15.5 mils) was drawn in two stages employing a glycerine draw bath under the conditions of 4× at 53° C. followed by 1.25× at 72° C. and subsequently water-washed and dried in vacuo at room temperature.

ANNEALING

The drawn monofilament was annealed at 80° C. for 6 hours with 5% relaxation.

EXAMPLE 23

The copolyester of Example 12 is made into monofilament suture material in accordance with the following extrusion, drawing, and annealing conditions:

EXTRUSION

The copolyester was spun at 155° C. at a shear rate of 213 sec$^{-1}$ using an INSTRON Capillary Rheometer with a 40 mil die (L/D=24.1) and a ram speed of 2 cm/min. An apparent melt viscosity of 5900 poise was observed. The fiber was taken up at 24 feet/minute after an ice water quench; the wound fiber was dried and subsequently drawn the next day.

DRAWING

The extrudate (diameter range: 18.5 to 19.5 mils) was drawn in two stages employing a glycerine draw bath under the conditions of 4× at 56° C. followed by 1.5× at 72° C. and subsequently water-washed and dried in vacuo at room temperature.

ANNEALING

The drawn monofilament was annealed at 80° C. for 6 hours with 5% relaxation.

EXAMPLE 24

The copolyester of Example 10 is made into monofilament suture material in accordance with the following extrusion, drawing, and annealing conditions:

EXTRUSION

The copolyester was spun at 170° C. at a shear rate of 213 sec$^{-1}$ using an INSTRON Capillary Rheometer with a 40 mil die (L/D=24.1) and a ram speed of 2 cm/min. An apparent melt viscosity of 8800 poise was observed. The fiber was taken up at 28 feet/minute after an ice water quench; the wound fiber was dried and subsequently drawn the next day.

DRAWING

The extrudate (diameter range: 16.0 to 18.0 mils) was drawn in two stages employing a glycerine draw bath under the conditions of 5× at 61° C. followed by 1.2× at 69° C. and subsequently water-washed and dried in vacuo at room temperature.

ANNEALING

The drawn monofilament was annealed at 80° C. for 6¼ hours with 5% relaxation.

The annealed monofilaments of Examples 22, 23, and 24 were cut to appropriate lengths, placed in individual paper folders and heat-sealable vented foil envelopes. The packages were subjected to 50° C. and 0.1 mm Hg pressure for 72 hours to dry and subsequently sealed under nitrogen. Portions of the packaged fibers were sterilized by exposure to 2.5 Mrads of gamma radiation from a Co$^{60}$ source. Representative properties of the dried annealed monofilaments, both before and after Co$^{60}$ sterilization are displayed below in Table IV. Control 1 (also packaged and Co$^{60}$ sterilized) is included for comparison purposes.

TABLE IV

| | Diam., Mils | Straight Tensile × $10^{-3}$, psi | Elong., % | Young's Mod. × $10^{-3}$, psi | Fiber I.V. |
|---|---|---|---|---|---|
| | | Before Co$^{60}$ Irradiation | | | |
| Ex. 22 | 6.2 | 60.9 | 42 | 163 | 1.62 |
| Ex. 23 | 7.8 | 57.0 | 61 | 175 | 1.53 |
| Ex. 24 | 7.4 | 56.8 | 47 | 111 | 1.67 |
| Control 1 | 7.8 | 70.9 | 39 | 310 | 1.60 |
| | | After Co$^{60}$ Irradiation | | | |
| Ex. 22 | 7.0 | 49.9 | 45 | 153 | 1.48 |
| Ex. 23 | 8.0 | 51.9 | 67 | 174 | 1.38 |
| Ex. 24 | 7.8 | 48.5 | 55 | 115 | 1.69 |
| Control 1 | 8.2 | 58 | 37 | 301 | 1.21 |

The in vivo breaking strength retention profiles of the sterilized monofilaments of Examples 22, 23, and 24 were determined. The results are displayed in Table V:

TABLE V

| | | In vivo BSR | |
|---|---|---|---|
| Sample | Initial Strength, lbs | BSR % 21 days | 28 days |
| Ex. 22 | 1.69 | 61 | 47 |
| Ex. 23 | 2.53 | 66 | 43 |
| Ex. 24 | 2.34 | 71 | 57 |
| Control 1 | 3.08 | 30 | 25 |

EXAMPLE 25

The copolyester of Example 16 is made into monofilament suture material in accordance with the following extrusion, drawing, and annealing conditions:

EXTRUSION

The copolyester was spun at 165° C. at a shear rate of 213 sec$^{-1}$ using an INSTRON Capillary Rheometer with a 40 mil die (L/D=24.1) and a ram speed of 2 cm/min. An apparent melt viscosity of 9100 poise was observed. The fiber was taken up at 24 feet/minute after an ice water quench; the wound fiber was dried and subsequently drawn the same day.

DRAWING

The extrudate (diameter range 16.0 to 19.5 mils) was drawn in two stages employing a glycerine draw bath under the conditions of 4× at 60° C. followed by 1.25× at 80° C. and subsequently water-washed and dried in vacuo at room temperature.

ANNEALING

The drawn monofilament was annealed at 80° C. for 6 hours with 5% relaxation.

EXAMPLE 26

The copolyester of Example 17 is made into monofilament suture material in accordance with the following extrusion, drawing, and annealing conditions:

EXTRUSION

The copolyester was spun at 170° C. at a shear rate of 213 sec$^{-1}$ using an INSTRON Capillary Rheometer with a 40 mil die (L/D=24.1) and a ram speed of 2 cm/min. An apparent melt viscosity of 2800 poise was observed. The fiber was taken up at 24 feet/minute after an ice water quench; the wound fiber was dried and subsequently drawn the next day.

DRAWING

The extrudate (diameter range: 17.5 to 19.5 mils) was drawn in two stages employing a glycerine draw bath under the conditions of 4× at 52° C. followed by 1.5× at 70° C. and subsequently water-washed and dried in vacuo at room temperature.

ANNEALING

The drawn monofilament was annealed at 80° C. for 6 hours with 5% relaxation.

The annealed monofilaments of Examples 25 and 26 were cut to appropriate lengths, placed in individual paper folders and heat-sealable vented foil envelopes. The packages were subjected to 50° C. and 0.1 mm Hg pressure for 72 hours to dry and subsequently sealed under nitrogen. Portions of the packaged fibers were sterilized by exposure to 2.5M rads of gamma radiation from a Co$^{60}$ source. Properties of the packaged monofilaments, both sterile and non-sterile, are displayed below in Table VI:

TABLE VI

| Sample | Diam., Mils | Straight Tensile, × $10^{-3}$, psi | Knot Tensile × $10^{-3}$, psi | Young's Mod., × $10^{-3}$, psi | Elong., % |
|---|---|---|---|---|---|
| | | Before Co$^{60}$ Irradiation | | | |
| Ex. 25 | 8.8 | 61.6 | 43.2 | 186 | 56 |
| Ex. 26 | 7.7 | 59.4 | 46.0 | 279 | 47 |
| | | After Co$^{60}$ Irradiation | | | |
| Ex. 25 | 8.1 | 62.5 | 53.5 | 160 | 57 |
| Ex. 26 | 7.7 | 54.6 | 45.7 | 272 | 51 |

The in vivo breaking strength retention profiles of the packaged monofilaments of Example 25 before and after Co$^{60}$ sterilization were determined. The results are displayed in Table VII:

TABLE VII

| | | In vivo BSR | | | |
|---|---|---|---|---|---|
| Sample | Initial Strength, lbs. | BSR % 7 | 14 | 21 | 28 (days) |
| Non-Sterile | 3.52 | 94 | 84 | 82 | 74 |
| Sterile | 3.12 | 91 | 79 | 72 | 57 |

GENERATION OF ABSORPTION DATA

Under aseptic conditions, two 2-centimeter segments of a suture sample are implanted into the left and right gluteal muscles of female Long-Evans rats. Two rats per period are implanted for each of the examination periods. The animals utilized in these studies are handled and maintained in accordance with the requirements for the Animal Laboratory Welfare Act and its 1970 Amendment. The rats are killed at the appropriate periods by carbon dioxide asphyxiation, then their gluteal muscles are excised and fixed in buffered formalin. Utilizing standard histologic techniques, H and E stained slides of the muscles and implanted sutures are prepared for microscopic examination. Utilizing an ocular micrometer, the approximate suture cross-sectional area is estimated in each site. The cross-sectional area at five days is used as the reference value for estimating percent cross-sectional area remaining at subsequent intervals.

EXAMPLE 27

The absorption profiles of gamma radiation sterilized suture material of Examples 20, 21, 22, 23, and 25 were determined; results are presented in Table VIII below:

TABLE VIII

Median Percent Suture Area Remaining After Intramusculer Implantation in Rats*

| SAMPLE | Days Postimplantation | | | | | | | |
|---|---|---|---|---|---|---|---|---|
| | 5 | 91 | 119 | 150 | 154 | 180 | 182 | 210 |
| EXAMPLE 20 | 100 | — | — | 28 | — | 1 | — | 0 |
| EXAMPLE 21 | 100 | — | — | — | 3 | — | 0 | 0 |
| EXAMPLE 22 | 100 | — | — | — | 0 | — | 0 | — |
| EXAMPLE 23 | 100 | — | — | — | 0 | — | 0 | — |
| EXAMPLE 25 | 100 | 100 | 87 | 0 | | , | | |

*The data represent the median of 7-8 cross sections in 2 rats per period per sample.

EXAMPLE 28

The copolyester of Example 18 is made into monofilament suture material in accordance with the following extrusion, drawing, and annealing conditions:

EXTRUSION

The copolyester was spun at 150° C. at a shear rate of 213 sec$^{-1}$ using an INSTRON Capillary Rheometer with a 40 mil die (1/D=24.1) and a ram speed of 2 cm/min. An apparent melt viscosity of 8058 poise was observed. The fiber was taken up at 24 feet/minute after an ice water quench; the wound fiber was dried and subsequently drawn the same day.

DRAWING

The extrudate (diameter range 18.0 to 20.0 mils) was drawn in two stages employing a glycerine draw bath under the conditions of 4× at 49° C. followed by 1.50× at 78° C. and subsequently water-washed and dried in vacuo at room temperature.

ANNEALING

The drawn monofilament was annealed at 80° C. for 6 hours with 5% relaxation.

EXAMPLE 29

The copolyester of Example 19 is made into monofilament suture material in accordance with the following extrusion, drawing, and annealing conditions:

EXTRUSION

The copolyester was spun at 155° C. at a shear rate of 213 sec$^{-1}$ using an INSTRON Capillary Rheometer with a 40 mil die (L/D=24.1) and a ram speed of 2 cm/min. An apparent melt viscosity of 7789 poise was observed. The fiber was taken up at 24 feet/minute after an ice water quench; the wound fiber was dried and subsequently drawn on the 14th day.

DRAWING

The extrudate (diameter range: 20.0 to 22.0 mils) was drawn in two stages employing a glycerine draw bath under the conditions of 5× at 60° C. followed by 1.2× at 80° C. and subsequently water-washed and dried in vacuo at room temperature.

ANNEALING

The drawn monofilament was annealed at 80° C. for 6 hours with 5% relaxation.

The annealed monofilaments of Examples 29 and 30 were cut to appropriate lengths, placed in individual paper folders and heat-sealable vented foil envelopes. The packages were subjected to 50° C. and 0.1 mm Hg pressure for 72 hours to dry and subsequently sealed under nitrogen. Portions of the packaged fibers were sterilized by exposure to 2.5Mrads of gamma radiation from a Co$^{60}$ source. Properties of the packaged monofilaments, both sterile and non-sterile, are displayed below in Table IX:

TABLE IX

| Sample | Diam., Mils | Straight Tensile × 10$^{-3}$, psi | Knot Tensile × 10$^{-3}$, psi | Young's Mod., × 10$^{-3}$, psi | Elong., % |
|---|---|---|---|---|---|
| | Before Co$^{60}$ Irradiation | | | | |
| Ex. 28 | 7.5 | 84.7 | 60.2 | 153 | 51 |
| Ex. 29 | 8.2 | 59.3 | 50.9 | 191 | 60 |
| | After Co$^{60}$ Irradiation | | | | |
| Ex. 28 | 7.7 | 69.2 | 49.5 | 144 | 53 |
| Ex. 29 | 8.0 | 54.0 | 50.0 | 189 | 55 |

A preferred utility of the copolyesters of the invention is the preparation of absorbable surgical filaments such as sutures and ligatures.

This utility has been illustrated in detail above. The utility of the surgical filaments of the invention is enhanced because said filaments can be sterilized by gamma radiation and still retain a useful level of physical properties, and because said filaments have a highly desirable combination of properties. One particularly interesting property exhibited by the subject filaments is relatively low Young's modulus, e.g., below 300,000 psi, which is an indication of good compliance, combined with acceptable straight tensile strength, e.g., above 40,000 psi. For instance, see the data presented in Table IV, above, in which filaments made from the subject copolyesters are compared with filaments made from p-dioxanone homopolymers. It has also been found that the copolyesters of the invention, in the form of surgical filaments, exhibit minimal tissue reaction after implantation in vivo. This is a highly desirable property of a material designed to be used as an absorbable surgical device.

While surgical filaments such as sutures and ligatures is the preferred utility for the subject copolyesters, other surgical devices can be fabricated from the copolyesters. Illustrative are absorbable films, membranes, fabrics, composites, and the like.

What is claimed is:

1. An absorbable, radiation sterilizable, normally solid polymer comprising a copolyester that comprises repeating divalent units of the formulas:

(A) —O—CO—CH$_2$—O—CH$_2$CH$_2$—, and (B) —G—, and (C) —O—CO—CHR—O)$_m$Ph—O—CHR—CO—O— wherein G represents the residue after removal of the hydroxyl groups of a dihydric alcohol, wherein Ph represents 1,2-, 1,3-, or 1,4- phenylene or alkyl- or alkoxy-substituted phenylene, wherein m represents a number having a value of 0 or 1, wherein each R individually represents hydrogen or lower alkyl, and wherein the divalent units (A), (B), and (C) are bonded to each other through ester groups contained in said units, wherein said polymer is produced by reacting p-dioxanone with a polyester comprising the repeating divalent units (B) and (C) as defined above.

2. The polymer of claim 1 wherein Ph represents 1,4-phenylene.

3. The polymer of claim 1 wherein Ph represents 1,3-phenylene.

4. The polymer of claim 1, 2, or 3 wherein G represents polymethylene of from 3 to 6 carbon atoms.

5. The polymer of claim 1, 2, or 3 wherein m is zero.

6. The polymer of claim 4 wherein m is zero.

7. The polymer of claim 1, 2, or 3 wherein m is one.

8. The polymer of claim 4 wherein m is one.

9. The polymer of claim 1 wherein the divalent units are of the formula:

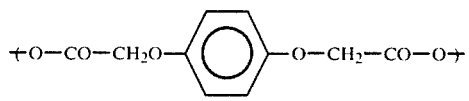

10. The polymer of claim 1 wherein the divalent units are of the formula:

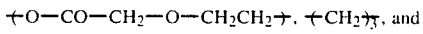

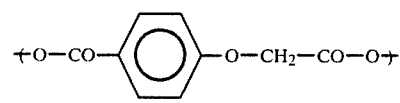

11. The polymer of claim 1 wherein the divalent units are of the formula:

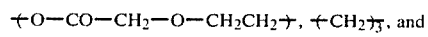

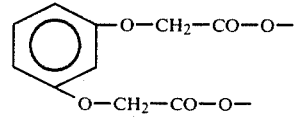

12. The polymer of claim 1 wherein the divalent units (A) constitute from about 59 to about 99 weight percent of the copolyester.

13. The polymer of claim 1 wherein the divalent units (A) constitute from about 75 to about 90 weight percent of the copolyester.

14. The polymer of claim 1, 2, 3, 9, 10, 11, 12, or 13 in the form of a fiber.

15. The polymer of claim 4 in the form of a fiber.
16. The polymer of claim 5 in the form of a fiber.
17. The polymer of claim 6 in the form of a fiber.
18. The polymer of claim 7 in the form of a fiber.
19. The polymer of claim 8 in the form of a fiber.

* * * * *